US006595756B2

(12) United States Patent
Gray et al.

(10) Patent No.: US 6,595,756 B2
(45) Date of Patent: Jul. 22, 2003

(54) ELECTRONIC CONTROL SYSTEM AND PROCESS FOR ELECTROMAGNETIC PUMP

(75) Inventors: John Gray, Woodland Hills, CA (US); Robert W. Bosley, Cerritos, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 10/033,721

(22) Filed: Dec. 27, 2001

(65) Prior Publication Data

US 2003/0049135 A1 Mar. 13, 2003

Related U.S. Application Data

(60) Provisional application No. 60/318,125, filed on Sep. 7, 2001.

(51) Int. Cl.⁷ .............................................. F04B 49/06
(52) U.S. Cl. ...................... 417/44.1; 417/53; 604/890.1
(58) Field of Search ................................ 604/131, 132, 604/140, 151, 141, 93.01, 65, 66, 67, 30, 31, 890.1, 891.1, 32; 417/44.1, 416, 417, 486, 487, 505, 53; 318/126

(56) References Cited

U.S. PATENT DOCUMENTS

| | | | |
|---|---|---|---|
| 4,193,397 A | | 3/1980 | Tucker et al. |
| 4,360,019 A | * | 11/1982 | Portner et al. .......... 128/213 R |
| 4,468,221 A | | 8/1984 | Mayfield |
| 4,636,150 A | | 1/1987 | Falk et al. |
| 4,692,673 A | * | 9/1987 | DeLong ...................... 318/132 |
| 4,715,852 A | * | 12/1987 | Reinicke et al. ............. 604/131 |
| 4,778,353 A | * | 10/1988 | Wiernicki ..................... 417/53 |
| 4,925,443 A | * | 5/1990 | Heilman et al. ............... 600/16 |
| 6,193,477 B1 | | 2/2001 | Falk et al. |
| 6,200,102 B1 | * | 3/2001 | Diaz ........................... 417/50 |
| 6,264,432 B1 | * | 7/2001 | Kilayko et al. ............. 417/44.1 |
| 6,264,439 B1 | * | 7/2001 | Falk et al. ................... 417/417 |

OTHER PUBLICATIONS

PCT International Search Report as issued in International Application No. PCT/US02/28023, Mailing date Jan. 2, 2003.

* cited by examiner

Primary Examiner—Charles G. Freay
Assistant Examiner—Han L. Liu
(74) Attorney, Agent, or Firm—Foley & Lardner

(57) ABSTRACT

An electronic control systems and process for infusion devices and pump configurations can provide highly efficient use of electrical power. The system may include a capacitor which is controlled to partially, but not fully discharge, to provide a power pulse to a pump coil. In this manner, the capacitor remains partially charged and need not be re-charged from a fully discharged state. In addition, the power applied to the coil in a given discharge pulse signal may be controlled to correspond to the power needs of the pump, by controlling the degree to which the capacitor is discharged to produce the pulse signal. A power cut-off switch may be provided to control the discharge of the capacitor such that the capacitor is stopped from discharging prior to the actual end of the armature stroke. The time at which the capacitor discharge is stopped may be selected such that energy remaining in the coil after the capacitor stops discharging is sufficient to continue the pump stroke to the actual end of the stroke. The time at which the capacitor discharge is cut off may be based on the location of the armature in its stroke motion. A power disconnect switch may be provided between the capacitor and the battery, to allow the capacitor to be electrically disconnected from the battery during storage or other periods of non-use, to avoid losing battery power due to the inherent leakage of the capacitor during prolonged periods of non-use.

58 Claims, 6 Drawing Sheets

ELECTRONIC CONTROL SYSTEM AND PROCESS FOR ELECTROMAGNETIC PUMP

CROSS-REFERENCE TO RELATED APPLICATIONS

Embodiments of the present invention claim priority from a U.S. Provisional Application entitled "ELECTRONIC CONTROL SYSTEM AND PROCESS FOR ELECTROMAGNETIC PUMP," Serial No. 60/318,125, filed Sep. 7, 2001, the contents of which are incorporated by reference herein.

FIELD OF THE INVENTION

The present invention relates generally to electronic control systems, configurations and processes for electromagnetic pumps and, in particular embodiments, to such systems, configurations and processes for efficient utilization of power and reduction of power consumption requirements in electromagnetic pumps. Further embodiments of the invention relate to electromagnetic pumps which employ such systems, configurations and processes and yet further embodiments relate to infusion devices and, more preferably, implantable infusion devices which employ electromagnetic pumps having such electronic control systems, configurations and processes.

RELATED ART

Infusion devices are typically used to deliver an infusion medium, such as a medication, to a patient. Implantable infusion devices are designed to be implanted in a patient's body to administer an infusion media to the patient at a regulated dosage, over a period of time. External infusion devices may be designed to be portable, for example, to be worn outside of a patient's body and connected to the patient by a catheter. Other forms of infusion devices are non-portable devices, typically for use in a controlled environment, such as a hospital.

Infusion devices typically include an electromagnetic pump mechanism that is operated to, selectively drive infusion medium to the patient. Various forms of electromagnetic pumps have been developed for use in infusion devices operating in external or implant environments. Examples of such pumps include those described in U.S. Pat. No. 4,594,058 to Fischell; U.S. Pat. No. 4,684,368 to Kenyon; U.S. Pat. No. 4,569,641 to Falk et al.; U.S. Pat. No. 4,568,250 to Falk, et al.; U.S. Pat. No. 4,636,150 to Falk, et al.; and U.S. Pat. No. 4,714,234 to Falk et al.

Typical electromagnetic pump configurations, such as those described in the above-referenced patents, employ a conductive coil coupled to a battery, through control electronics. The coil is selectively energized by the power source and control electronics to create an electromagnetic field which operates on a moveable armature. When the coil is energized, the electromagnetic field causes the armature to move against the force of a spring, toward a stroke position. When the coil is then de-energized, the mechanical spring force returns the armature to the position it had prior to energizing the coil. By moving the armature between its energized stroke position and its return position, a pumping action is accomplished.

In some contexts of use, infusion devices may be operable for an extended period with a limited power supply. For example, battery powered infusion devices may be implanted in or otherwise connected to patients, to deliver medication at controlled intervals over a prolonged period of time. As the battery power supplies have limited capacities, such devices may require multiple replacements of batteries over their operational life. In the case of an implanted infusion device, a replacement of a battery may require the surgical removal of the infusion device. Even with external devices, the replacement of a battery may require specialized tools, parts or skills which necessitate the services of a specialist or trained technician. Thus, a patient requiring a battery replacement may experience inconveniences and costs associated with seeing specialists, while implant patients may further experience the risks, trauma and costs of surgery. Accordingly, there is a demand in the industry for infusion devices which make efficient use of power supplies and, thus, require fewer power supply replacements. This demand is particularly important for implantable devices.

Prior infusion device pumps, such as the P650005 made by Wilson Greatbatch, Ltd., employ capacitor-discharge power control circuits. Such power control circuits include a capacitor that is charged by a battery and discharged to a coil, to power the pump operation. In one representative example, such power control circuits employ a 47 micro-Farad capacitor which is charged at about 16 volts. Each complete discharge of the capacitor delivers an electric power pulse to the coil sufficient to energize the coil and cause the pump to make one complete stroke. The capacitor is fully charged by the battery between pump stokes.

Because a given capacitor charged to a given voltage level produces a fixed amount of power per complete discharge, the pump receives a fixed amount of power independent of the pump's power needs. However, the power requirements of the pump can vary due to many different factors, such as the formation of partial blockages in the flow path, changes in atmospheric pressure (which may occur, for example, if a patient travels to a high altitude location or swims or dives under water), or changes in the volume of stored infusion medium.

In order to operate the pump under all expected power load conditions, the capacitor size in such prior devices is selected such that the power output per complete discharge is sufficient to operate the pump in the greatest expected power load condition. As a result, sufficient power to operate the pump in the greatest expected load condition is provided to the pump, even when the pump is not operating under the greatest expected load. Such a power discharge at every pump operation, independent of the pump's power needs, results in a significant waste of electric power.

Accordingly, there is a demand in the industry for electronic power control systems and processes for electromagnetic pumps which provide sufficient power to operate the pump under varying load conditions, but which minimize or decrease power consumption requirements as compared to prior power control systems. There is a further need in the industry for electromagnetic pump configurations which minimize or reduce power consumption requirements as compared to prior pump configurations.

SUMMARY OF THE DISCLOSURE

Embodiments of the present invention relate to electric power control systems and processes, infusion devices and pumps for infusion devices which address the above-mentioned industry demands.

Embodiments of the invention relate to electronic control systems and process, infusion devices and pump configurations for highly efficient use of electrical power. Preferred embodiments relate to such power efficient systems and processes for prolonged operational life with a depletable power source, such as, for example, a battery. Several aspects and features of electronic power control systems and processes and pump configurations described herein allow reduced or minimized power consumption requirement for a given infusion output volume. Various embodiments of the invention include one or more of such aspects and features for improved power consumption efficiency.

Preferred embodiments of the invention relate to electronic control systems and process, infusion devices and pump mechanisms configured for implantation in a patient's body. Further preferred embodiments employ power consumption efficiency aspects and features referenced above to provide improved operational life within an implant environment.

Yet further preferred embodiments relate to such devices and pump mechanisms configured to deliver relatively precisely controlled volumes of infusion medium, within a relatively wide range of volumes, including relatively small volumes.

Yet further preferred embodiments relate to such devices and pump mechanisms configured to deliver sufficiently precise volumes of relatively high concentration infusion medium.

An infusion device according to an embodiment of the invention includes a generally disc-shaped housing made from a biocompatible material. The housing contains a reservoir for holding a volume of infusion medium, such as, but not limited to, a medication to be administered to the patient. The housing has an outlet through which the infusion medium may be expelled. The reservoir is coupled in fluid flow communication with the outlet.

The infusion device also includes or operates with a pump mechanism coupled in fluid flow communication with the reservoir. The infusion device further includes or operates with an electronic power control system for controlling and providing electronic power to the pump mechanism.

A pump mechanism, according to preferred embodiments, employs electromagnetic and mechanical forces to move between retracted (or quiescent) and forward states, to cause infusion medium to be drawn from the reservoir, through an inlet and forced out of an outlet. A preferred pump configuration includes a housing containing an electrical coil disposed within a core or coil cup made of magnetizable material, a piston extending through an axial channel in the coil and coil cup, an armature disposed at one end of the axial channel and an outlet chamber with a valve assembly disposed at the other end of the axial channel. Other suitable pump configurations may be employed in other embodiments.

In the quiescent state, the piston and armature are urged toward a retracted position. When the coil is energized, an electromagnetic field generated by the coil draws the armature toward the coil cup. As a result, the armature and piston move to a forward stroke position. The movement of the piston between retracted and forward positions creates pressure differentials within the internal chambers and volumes of the pump device, to draw infusion medium into the inlet and drive medium out the outlet.

A power control system, according to preferred embodiments of the invention, is configured for highly efficient use of electrical power by the pump mechanism. According to one preferred embodiment, a power control system comprises a capacitor circuit having a capacitor which is controlled to partially, but not fully, discharge to provide a power pulse to a pump coil. In this manner, the capacitor remains partially charged and need not be re-charged from a fully discharged state. In addition, the power applied to the coil in a given discharge pulse signal may be controlled to correspond to the power needs of the pump, by controlling the degree to which the capacitor is discharged to produce the pulse signal.

According to a further preferred embodiment, the power control system has a power cut-off switch to control the discharge of the capacitor such that the capacitor is stopped from discharging prior to the actual end of the armature stroke. In yet further preferred embodiments, the time at which the capacitor discharge is stopped is selected such that energy remaining in the coil after the capacitor stops discharging is sufficient to continue the movement of the armature to the actual end of the armature stroke. The time at which the capacitor discharge is cut off may be based on the location of the armature in its stroke motion. According to one embodiment, electromotive force (EMF) generated in the coil is monitored to determine a suitable time to stop discharging the capacitor. According to a further embodiment, a suitable time to cut off the capacitor discharge is pre-selected and set, based on observed pump operations at various capacitor shut-off times.

According to yet further preferred embodiments, a power disconnect switch is provided between the capacitor and the battery, to allow the capacitor to be electrically disconnected from the battery during storage or other periods of non-use. In this manner, the system may avoid losing battery power due to the inherent leakage of the capacitor during prolonged periods of non-use.

In yet further preferred embodiments, a detector is provided to detect the pressure differential between the inlet and outlet of the pump mechanism and the power control system adjusts the power applied to the coil based on the detected pressure differential, for example, by controlling the capacitor shut-off time. In this manner, the power control system may apply more power, for example, by providing a longer capacitor discharge period when the detected pressure differential increases, and less power or a shorter discharge period when the detected pressure differential decreases. In further preferred embodiments, a detector is provided to detect the battery voltage and the power applied to the coil by the power control system is adjusted based on the detected battery voltage. In this manner, the power applied to the coil may be reduced to conserve battery life, for example, by reducing the capacitor discharge period, as the battery voltage level decreases.

According to further preferred embodiments, the pump mechanism includes one or more features relating to structural configurations for improved power consumption efficiency. Such features include pole configurations, where the ratio of the surface areas of inner and outer pole surfaces is selected to improve power consumption efficiency. Another feature comprises pole interfaces which provide a gap between the outer pole surfaces that is greater than a gap between the inner pole surfaces, where the ratio of the gaps of inner and outer pole surfaces is selected to improve power consumption efficiency. Another feature comprises the aspect ratio of the coil which may be selected to improve power consumption efficiency. Yet another feature comprises an armature configuration with magnetically conductive material forming radial flux paths and fluid passages therebetween, where the fluid passages reduce fluidic resistance as the armature is moved during a pump stroke. Yet another feature comprises an armature configuration with magnetically conductive material forming radial flux paths without fluid passages therebetween.

Another manner of improving the operational life of an infusion device according to embodiments of the invention is to reduce the number of operations of the drive mechanism required over a given period of time, by pumping reduced volumes of a higher concentration infusion medium (an infusion medium with a higher concentration of active ingredients) or pumping higher concentration volumes at reduced intervals. Accordingly, a number of aspects and features relating to the power control system and pump mechanism described herein can provide, or be combined to contribute to the efficient use of power, to, thereby, prolong the operational life of an electromagnetic pump mechanism.

These and other aspects and advantages of the invention will be apparent to one of skill in the art from the accompanying detailed description and drawings.

BRIEF DESCRIPTION OF THE DRAWINGS

Referring now to the drawings in which like reference numbers represent corresponding parts throughout.

DETAILED DESCRIPTION OF PREFERRED EMBODIMENTS

The following detailed description is of the best presently contemplated mode of implementing the invention. This description is not to be taken in a limiting sense, but is made merely for the purpose of illustrating the general principles of the invention. The scope of the invention is best defined by the appended claims.

As discussed above, the present invention relates generally to electronic control systems, configurations and processes for electromagnetic pumps. Preferred embodiments of the invention relate to such systems, configurations and processes for efficient utilization of power and reduction of electrical power consumption requirements in electromagnetic pumps. Further embodiments of the invention relate to electromagnetic pumps which employ such systems, configurations and processes. Yet further embodiments relate to infusion devices and, more preferably, implantable infusion devices which employ electromagnetic pumps having such electronic control systems, configurations and processes.

Figure 1:
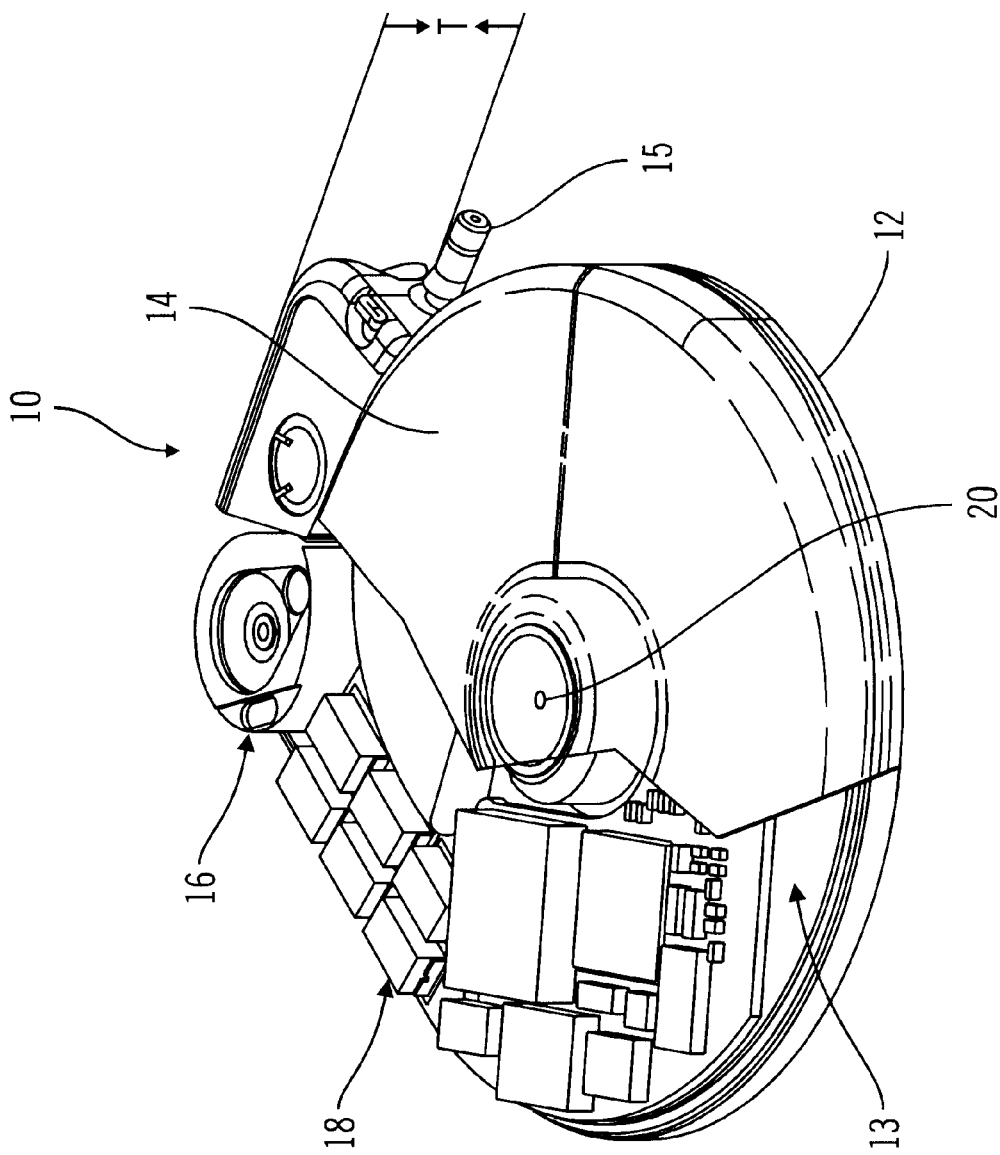
FIG. 1 is a perspective view of an implantable infusion device according to an embodiment of the invention.

FIG. 1 shows an implantable infusion device 10 according to an embodiment of the invention. The illustrated device 10 is configured as a single unit, containing an infusion medium reservoir, a pump mechanism, a power source and an electronic power control system, in a single, relatively compact package or housing 12. However, other embodiments may employ reservoirs, pump mechanisms, power sources and control systems in multiple, discrete units, operatively connected together by suitable conduits.

The device 10 may be configured to be surgically implanted into a patient, for example, at a particular location in the venous system, along the spinal column, in the peritoneal cavity, or other suitable site to deliver an infusion medium to the patient. As described below, preferred embodiments of the device 10 are configured in accordance with one or more aspects of the invention for enhancing efficient usage of electronic power and prolonged usage once implanted. However, further embodiments of the invention may be implemented as external infusion devices, which connect to patients through suitable catheter devices or the like. Yet further embodiments of the invention may be used in other contexts, for delivery of a medium into other suitable environments. Therefore, for purposes of simplifying the present disclosure, the term "patient" is used herein to refer to the entity or environment in which an implantable device is implanted or to which an external device is connected, whether or not the implant or connection is carried out for medical purposes.

The illustrated device 10 includes a generally disc-shaped housing 12. While a generally circular disc-shaped embodiment is illustrated in FIG. 1, it will be understood that further embodiments of the invention may employ housings of other shapes, including, but not limited to, oval, oblong, rectangular, or other curved or polygonal shapes.

The housing 12 includes a reservoir housing portion 13 containing a reservoir for holding a volume of infusion medium, such as, but not limited to, a liquid medication to be administered to the patient. The housing 12 includes a further housing portion 14, located above the reservoir housing portion 13 in the orientation shown in FIG. 1, for containing a drive mechanism, a power source and control electronics described below.

Representative examples of reservoir housing portions and reservoirs which may be employed in embodiments of the invention are described in co-pending U.S. patent application Ser. No. 60/317,880 (attorney docket no. 047711.0202), titled "Infusion Device and Reservoir For Same," which is incorporated herein by reference. However, further embodiments may employ other suitable reservoir configurations, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

The housing 12 also has an outlet 16 through which the infusion medium may be expelled. When the device 10 is implanted in a patient or connected externally to a patient, a catheter may be connected to the outlet 16, to deliver infusion medium expelled from the outlet 16 into the patient's blood stream or to a selected location in the patient's body. The infusion device 10 may also include an inlet structure 18 which provides a closeable and sealable fluid flow path to the reservoir in the reservoir portion 13 of the housing. The inlet structure provides a port for receiving a needle through which fluid may be transferred to the infusion device, for example, to fill or re-fill the reservoir of the device. In preferred embodiments, the inlet structure is configured to re-seal after a fill or re-fill operation, and to allow multiple re-fill and re-seal operations. One example of an inlet structure is described in co-pending U.S. patent application Ser. No. 60/318,056 (attorney docket no. 047711.0203), titled "Infusion Device and Inlet Structure For Same," which is incorporated herein by reference. However, further embodiments may employ other suitable inlet structures, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

The infusion device 10 includes a pump or drive mechanism 20 located in the housing portion 14 and connected between the reservoir and the outlet 16, for driving infusion medium from the reservoir, through the outlet. The infusion device 10 further includes an electronic power control system 22 located in the housing portion 14. The electronic power control system 22 includes or operates with an electric power source, such as a battery, and control electronics for controlling the pump mechanism 20 to deliver infusion medium from the reservoir, to the patient in a selected manner. The pump mechanism may be controlled to deliver infusion medium in any suitable manner, for example, according to a programmed dispensing rate or schedule, or according to an actuation signal from a sensor, timer or other suitable source.

In implantable embodiments, the portion 14 of the housing 12 that contains the drive mechanism 20 and control electronics 22 is preferably hermetically sealed from the external environment and from the reservoir housing portion 13, while the reservoir housing portion 13 need not be hermetically sealed. In such an embodiment, the housing portion 14 containing the drive mechanism 20 and control electronics 22 may be made from titanium or titanium alloy or other biocompatible metals, while the reservoir portion 13 of the housing may be made from such metals or a biocompatible plastic.

As described above, a number of aspects relating to the power control system and pump mechanism configurations and operation are described herein which can individually enhance, or be combined to further enhance, the efficient use of power. One or more of such aspects or features may be employed in various embodiments of the invention.

As described in more detail below, pump mechanisms according to preferred embodiments of the invention employ electromagnetic and mechanical forces to move between retracted (or quiescent) and forward stroke states, to cause infusion medium to be drawn from the reservoir, through a pump inlet and forced out of a pump outlet. Such electromagnetic forces are generated by the application of an electrical power signal to a coil which, when energized, operates on an actuator composed of an armature and a piston. In the retracted state, the actuator is mechanically urged toward a retracted position. When the coil is energized, the actuator moves to a forward stroke position. The movement of the actuator between retracted and forward states creates pressure differentials within the internal chambers and volumes of the pump device, to draw infusion medium from the reservoir into the pump inlet and drive medium out of the pump outlet.

In preferred embodiments, the pump mechanism 20 has a structure and operation according to embodiments as described in co-pending U.S. patent application Ser. No. 60/317,886 (attorney docket no. 047711.0204), titled "Infusion Device And Driving Mechanism For Same," which is incorporated herein by reference. An example of that type of pump mechanism 20 is described below with reference to FIGS. 6–8. However, further embodiments may employ other suitable pump or drive mechanism configurations.

Figure 2:
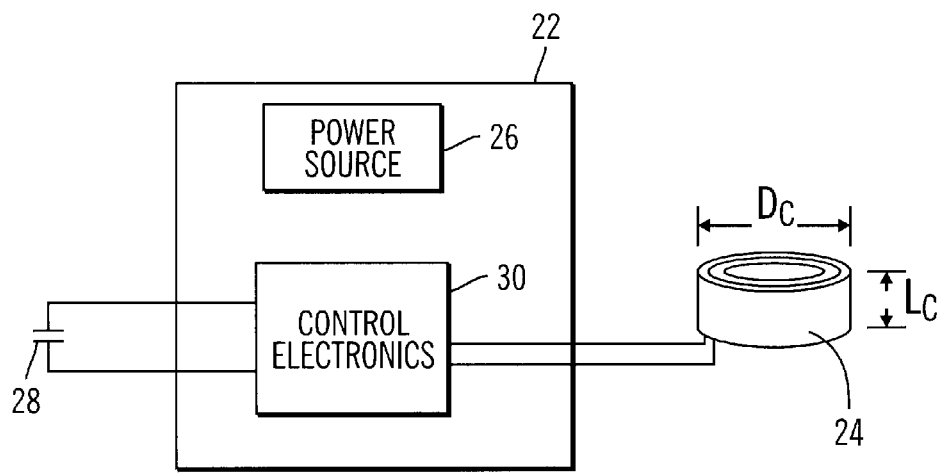
FIG. 2 is a generalized block diagram of a power control system and pump coil according to an embodiment of the invention.

FIG. 2 shows a generalized representation of a pump mechanism coil 24 electrically connected to a power control system 22, according to an embodiment of the invention. The power control system 22 includes or employs a power source 26, a power capacitor 28 and control electronics 30. In the illustrated embodiment, the power source 26, capacitor 28 and control electronics 30 are shown as part of a power control system 22 which may be implemented, for example, on a single circuit board. In other embodiments, the power source, capacitor and/or some of the control electronics may be implemented as discrete units, electronically connected together for operation.

In preferred embodiments, the power source 26 comprises a portable, depletable power storage device, such as a battery. The use of portable power sources, such as batteries, may be advantageous in contexts in which the pump mechanism is intended to be portable, such as in implanted or portable external infusion devices. However, other embodiments may employ other forms of power sources suitable for other contexts of use, including non-portable and nondepleting power sources.

The power source 26 is connected to charge the capacitor 28, while the capacitor 28 is connected to selectively discharge power to the coil 24. Because the internal impedance of the capacitor 28 may be much smaller than that of a battery or other form of a power source 26, the charged capacitor 28 can provide a faster response time than a direct connection of the power source 26 to the coil 24. More specifically, the charged capacitor 28 can provide a quick response power pulse to the coil 24, on demand.

The control electronics 30 controls the charging and discharging of the capacitor and may provide additional functions as described herein. The control electronics may comprise one or more programmable processors, logic circuits, or other hardware, firmware or software components configured for implementing functions described herein. Example hardware implementation of control electronics are described herein with respect to FIG. 3. However, other embodiments may employ other suitable hardware, firmware or programmable processor implementations of the control electronics 30.

Figure 3:
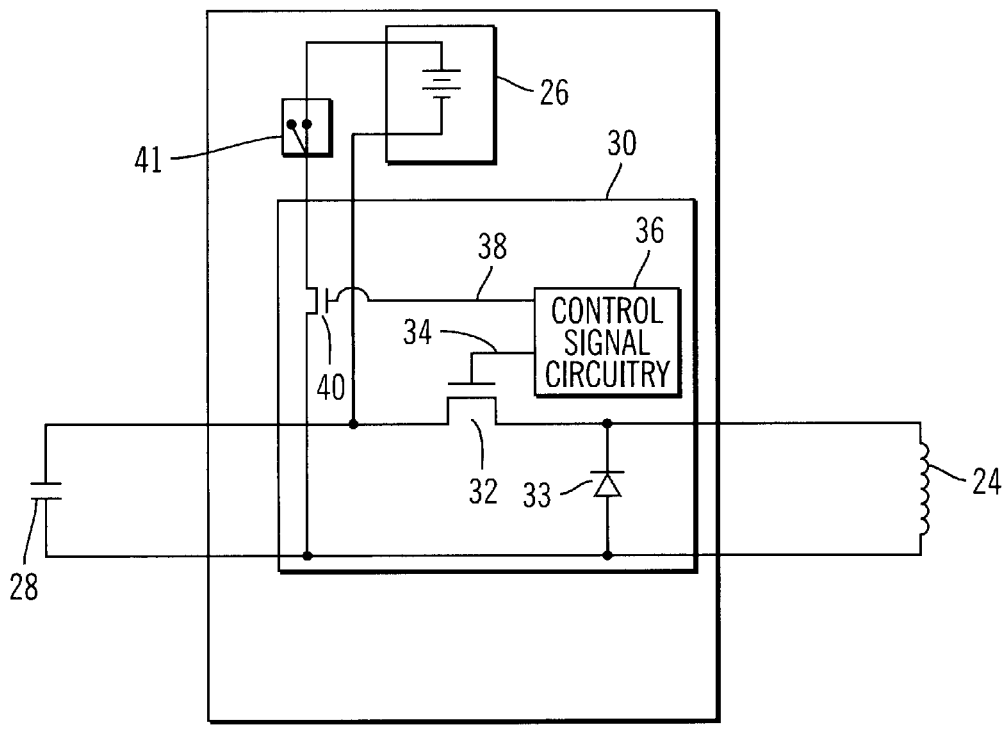
FIG. 3 is a generalized circuit diagram of an example of the power control system of FIG. 2.

The power control electronics 30 controls the discharge of power from the capacitor 28, to the coil 24, as needed or desired for operating the pump mechanism, by selectively coupling or de-coupling the capacitor to the coil. One example of a generalized electrical schematic for implementing such control functions is shown in FIG. 3. In the FIG. 3 embodiment, the capacitor 28 is connected to the coil 24, through an electronic switch device 32. A diode circuit 33 connected in parallel with the coil 24, or other suitable circuit may be provided to clamp the voltage across the coil 24 to a pre-defined value, when the switch device 32 is opened. As a result, diode circuit 33 allows current to continue to flow through the coil 24, for a period of time after the switch device 32 is opened. The diode circuit 33, thus, allows the coil to continue to provide an electromagnetic force to help the actuator reach the end of its forward stroke, even if the switch device 32 is opened before the actuator reaches the end of its forward stroke, as described below. In addition, the diode circuit 33 may inhibit the capacitor 28 from reversing polarity.

In one preferred embodiment, the diode circuit 33 comprises a Schottky diode connected as a flyback diode. In further embodiments, the diode circuit 33 can be replaced with a switch device, such as a field effect transistor (FET) or a junction transistor that is controlled (for example, by control signal circuitry 36) to close when switch device 32 is opened and to open when switch device 32 is closed.

In preferred embodiments, the electronic switch device 32 comprises a Field Effect Transistor (FET) which is controlled by a control signal line 34. Other embodiments may employ other suitable electronic or electromagnetic switch configurations, junction transistors, relays or the like as the switch device 32. By applying a control signal onto control signal line 34, the switch device 32 may be closed to connect the capacitor to the coil and allow the capacitor to discharge electrical current to the coil.

A control signal for operating the switch 32 may be applied to the control line for example, according to a programmed dispensing rate or schedule, or according to an actuation signal from a sensor, timer, manual operator or other suitable means. In the generalized schematic of FIG. 3, a control signal is selectively applied to the control signal line 34 by control signal circuitry 36. In this manner, the control signal circuitry 36 controls the switch device 32 to selectively close or open and, thus, to selectively couple or decouple the capacitor 28 to the coil 24. The control signal circuitry may comprise a dedicated processor, a programmable processor, logic circuitry or other hardware, firmware or combinations thereof, configured to provide control signal functions described herein.

The control signal circuitry 36 may also provide a control signal on a signal line 38 for operating a switch device 40 located between the power source 26 and the capacitor 28, to selectively control the charging of the capacitor 28 from the power source. The switch device 40 may be of any suitable form, such as described above with respect to switch device 32 and, in preferred embodiments, is a FET device. By applying a suitable signal on signal line 38, the switch device 40 may be selectively closed to charge the capacitor 28.

In one example embodiment, the control signal circuitry 36 is programmed or configured to generate a signal to control the closure of the switch device 32 upon the occurrence of one or more events. Such events may include the expiration of a predetermined time period, the detection of a need for infusion medium in the infusion environment, the manual operation of an operator switch, or the like. In this manner, the control circuitry 36 may be operatively connected to, or include, a timer to detect the expiration of the predetermined time period and apply a control signal on line 34 in accordance with that detection. Alternatively or in addition, the control circuitry 36 may be connected to, or include, a sensor for detecting conditions in the infusion environment, and/or to a manually operable switch for activating the processor to generate a control signal on line 34.

The control signal circuitry 36 may be included in the control electronics 30, as shown in FIG. 3, or may be implemented as a separate device, electrically connected to the control electronics 30. The control signal source 36 may be connected to the power source 26 for its power needs. Alternatively, the control signal source 36 may be provided with a separate power source (not shown).

Upon closure of the switch device 32, the capacitor 28 is electrically coupled to the coil 24. If the capacitor 28 is charged when the switch device 32 closes, the charged capacitor 28 will discharge current to energize the coil 24. As discussed above, when the coil is energized, the pump actuator is caused to move to a forward stroke position, against a mechanical spring force. The actuator may abut a stop surface or the like, at the actual end of the forward stroke.

Upon opening of the switch device 32, the capacitor 28 is electrically de-coupled from the coil 24. After the switch device 32 is opened, energy in the coil 24 dissipates and the mechanical spring force returns the actuator to its retracted position. The switch device 40 may then be closed to allow the capacitor 28 to re-charge for the next pump stroke operation. In this manner, the capacitor is controlled to charge and discharge to provide electrical energy to the coil 24, as needed to effect a pump stroke operation.

Figure 4:
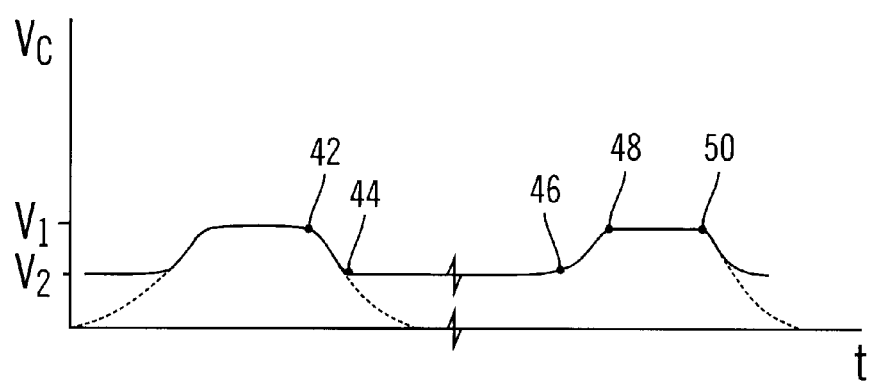
FIG. 4 is a graphical diagram of example voltage characteristics of a power discharge capacitor controlled according to an embodiment of the present invention.

According to a preferred embodiment, the capacitor 28 is controlled to partially, but not fully discharge to effect a pump stroke operation. A graph of an example voltage diagram for a capacitor 28 is shown in FIG. 4. With reference to FIG. 4, the voltage $V_c$ across the capacitor 28 rises during charging to its fully charged level $V_1$. To effect a pump stroke operation, the control signal circuitry 36 closes (turns ON) switch device 32 at point 42 in FIG. 4.

Once the switch device 32 is closed (ON), the capacitor 28 discharges and the voltage $V_c$ drops. However, prior to the capacitor reaching a fully discharged state, the control signal circuitry 36 opens (turns OFF) the switch device 32, for example, at point 44 in FIG. 4. The broken line portion of FIG. 4 shows the voltage across the capacitor 28, had the switch device 32 remained closed (ON) to completely discharge the capacitor. However, because the switch device 32 is opened (turned OFF) prior to full discharge of the capacitor 32, the voltage $V_c$ across the capacitor remains at a level $V_2$, above the fully discharged level.

While some leakage may occur before the next charging operation, the voltage across the capacitor 28 is at about the level $V_2$ or slightly lower, at point 46 in FIG. 4 when switch 40 is closed (turned ON) to re-charge the capacitor. Once the capacitor is fully charged, as shown at point 48 in FIG. 4, the switch 40 may be opened (turned OFF) and, as shown at point 50, the switch 32 may be closed (turned ON) to effect another pump operation. Thus, by controlling the capacitor to discharge partially, but not fully, for each pump stroke operation, the voltage across the capacitor 28 may have a characteristic similar to that shown in FIG. 4.

Because the voltage $V_c$ across the capacitor 28 remains at or about the level $V_2$ (above the fully discharged level) after its discharge, the amount of electrical energy and time needed to re-charge the capacitor 28 to the level $V_1$ is less than would be required, had the capacitor 28 been fully discharged. By selecting the size of the capacitor 28 and the levels $V_1$ and $V_2$, suitable power may be provided to the coil 24 during the discharge period (between points 42 and 44) to effect a pump stroke operation, while significant power savings may be achieved during the re-charging period (between points 46 and 48) as compared to charging a fully discharged capacitor. In addition, because the capacitor 28 remains partially charged at the end of its discharge period, the energy level of the capacitor 28 remains high enough to effect the operation of the pump mechanism, throughout the partial discharge period, including the end point 44 of the discharge period. Furthermore, because a partial charge remains at the end of the normal discharge period, the capacitor may be controlled to continue to discharge and provide additional discharge power beyond the end of a normal discharge period, in the event that additional power is needed by the pump mechanism.

The capacitor size and voltage levels will depend upon the characteristics and power needs of the pump mechanism.

However, preferred values suitable, for example, for use with an implantable infusion device, may include a capacitor size of between about 500 micro Farad and about 3000 micro Farad, and voltage levels for $V_1$ of between about 1.8 volts and about 5.0 volts and for $V_2$ of between about 40% and about 90% of $V_1$.

According to a further preferred embodiment, the point 44 at which the capacitor 28 stops discharging power to the coil 24 is controlled to occur at or, more preferably, prior to the actual end of the actuator stroke of the pump mechanism. As discussed above, when the coil is energized, the pump actuator is caused to move to a forward stroke position and may abut a stop surface or the like, at the actual end of the forward stroke. If the capacitor 28 continues to discharge power to the coil 24 after the actuator reaches the end of its stroke, such continued discharge of power will not produce any further movement of the pump actuator and, thus, will be wasted. Accordingly, to avoid undue waste of power, the capacitor discharge, according to preferred embodiments of the invention, is stopped (or cut off) at or prior to the actual end of the actuator stroke.

In embodiments in which the capacitor discharge is stopped (or cut off) prior to the actual end of the actuator stroke motion, the cut-off point 44 is selected to be at a point in time when sufficient energy remains in the coil 24 to cause the actuator to continue to move to the actual end of its stroke. More particularly, current applied to the coil 24 from the capacitor 28 during the capacitor discharge period (between points 42 and 44) creates electromagnetic energy within a flux path formed around the coil. Immediately after the capacitor cut-off point 44, residual inductively stored energy dissipates over a short period of time. The use of a flyback diode arrangement, as described above with respect to diode circuit 33, can increase the period of time in which such residual energy is dissipated. Thus, according to such further preferred embodiments of the invention, the residual energy is used to complete the actuator stroke motion after the capacitor cut-off point 44. The cut-off point may be selected such that the residual energy in the coil and the momentum of the actuator is about just enough or, more preferably, a selected amount greater than required, to complete the stroke motion of the actuator.

Figure 5:
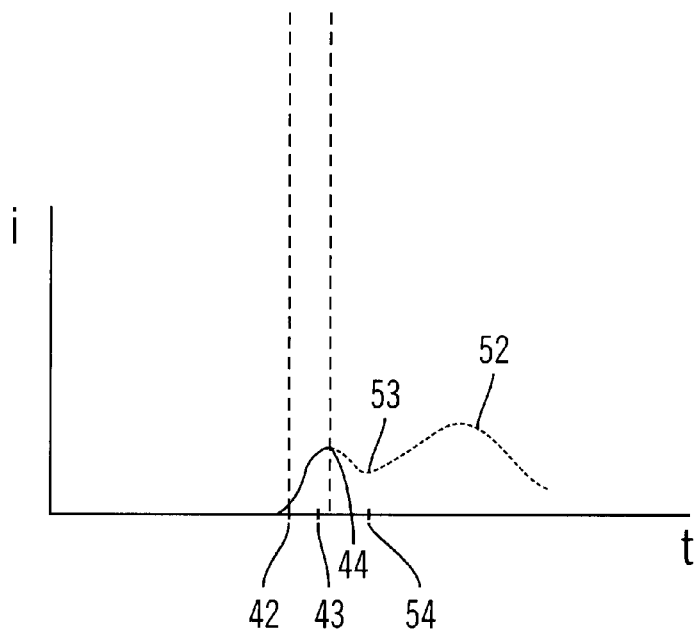
FIG. 5 is a graphical diagram of example current characteristics of a coil connected to a power discharge capacitor controlled according to an embodiment of the present invention.

For example, FIG. 5 shows a graphical representation of the coil current. In FIG. 5, the solid line represents current applied to the coil by the discharging capacitor. Using reference characters corresponding to those shown in the voltage graph of FIG. 4, the current graph of FIG. 5 shows the point 42 at which the capacitor begins discharging current to the coil. A period of time prior to point 42 may involve a circuit warm-up period. Point 44 in FIG. 5 represents the time at which the capacitor is cut off. As shown by the broken line 52 in FIG. 5, residual current in the coil dissipates over a period of time after the cut-off point 44 is reached. By suitable selection of the cut-off point 44, the residual current can provide sufficient energy to continue to move the actuator to its actual end of stroke position, represented as point 54 in the FIG. 5 embodiment. In some embodiments, it may be desirable to have a greater assurance that the actuator will reach the actual end of its stroke. This may be achieved by selecting the cut-off point 44 to be beyond a point 45 at which the residual energy in the coil and the actuator momentum would, under normal circumstances, carry the actuator to the actual end of its stroke.

A capacitor cut-off point 44 suitable to provide sufficient residual energy to move the actuator to its actual end of stroke may be selected in any suitable manner. According to one embodiment of the invention, the capacitor cut-off point 44 is selected, based on the location of the actuator in its stroke motion. For example, a suitable cut-off point 44 may be determined by repeated trial operation of a pump mechanism at various capacitor cut-off times, to observe when or where, in the course of the actuator motion, sufficient actuator momentum and residual coil energy is present to cause the actuator to complete its full stroke motion after the capacitor is cut off. Alternatively or in addition, position sensors may be employed with the actuator, to determine when or where, in the course of the actuator motion, the actuator is capable of completing its full stroke motion after the capacitor is cut off.

In one preferred embodiment, the back electromagnetic force (back EMF) of the coil 24 is detected to determine when or where, in the course of the actuator motion, the actuator is capable of completing its full stroke motion after the capacitor is cut off. More specifically, the current and back EMF in the coil change as a function of the actuator's position in its stroke motion. By detecting or monitoring the back EMF generated in the coil, a suitable cut-off time 44 may be determined. Electronics for detecting or monitoring the coil back EMF may be included in, or connected to, the control circuitry electronics 36. In one preferred embodiment, the capacitor 28 is selected to have a relatively low impedance, to enhance the detectability of changes in current. A sharp positive rise or a change in direction of the current graph of FIG. 5 (as shown at point 53) can indicate actuator deceleration that occurs at the actual end of the actuator's forward stroke.

According to another embodiment a suitable capacitor cut-off point 44 is determined by repeated trial operation of a pump mechanism at various capacitor cut-off times, to observe the pump output volume for each cut-off time. A cut-off point that delivers a volume within a predefined threshold range or level below the maximum observed output volume, may be selected. Thus, for example, repeated trial operations may be conducted to find a cut-off time that delivers an observed pump output volume within ten percent or, more preferably, two percent, of the maximum observed volume. Other embodiments may employ other suitable threshold ranges or levels to define the cut-off point.

In embodiments described above, the actual end of the actuator stroke is determined or predicted to select a capacitor cut-off point 44 that occurs prior to the actual end of the stroke. However, further embodiments may employ a cut-off point 44 selected to be at about the determined or predicted actual end of stroke position. Preferably, the cut-off point 44 is selected to avoid or reduce wasted energy consumption beyond the actual end of the actuator's stroke to, improve power consumption efficiencies.

In yet further preferred embodiments, the pump mechanism operation is controlled, based in part on the pressure differential between the inlet pressure and the outlet pressure of the pump mechanism. In such embodiments, a detector is provided to detect the pressure differential between the inlet and outlet of the pump mechanism.

According to one example embodiment, the detector may comprise an electronic circuit for detecting power, current, voltage or the like, required to move the actuator to its actual end of stroke. The detected value may be compared to an historical value, a threshold or the like, to determine whether the pump operation should be adjusted. For example, the control electronics 30 may include a processor and associated memory programmed or configured to store one or more values representing the power, current or voltage from one or more previous forward strokes of the pump mechanism. Alternatively or in addition, the stored values may represent pre-selected threshold values In response to a detected value being above or below a historical or threshold value, the control electronics adjusts one or more operating parameters of the pump mechanism. Other embodiments may employ other suitable detectors for detecting pressure differentials, including, but not limited to diaphragms connected to strain or deflection detectors, mechanical or Bernoulli pressure detection devices, or the like.

According to one embodiment, the power control electronics 30 adjusts the power applied to the coil based on the detected pressure differential, for example, by controlling the capacitor shut-off point 44, as discussed above. In this manner, the power control system may apply more power, for example, by providing a longer capacitor discharge period when the detected pressure differential increases, and less power or a shorter discharge period when the detected pressure differential decreases. As a result, more energy is drawn from the power source 26 only when needed to overcome higher pressure differentials, and less energy is drawn when the pressure differential is lower.

According to a further embodiment, the power control electronics 30 adjusts the time between forward strokes of the pump mechanism based on the detected pressure differential. In this manner, as the detected pressure differential increases, the power control system may allow more time between strokes to allow enough time for fluid to pass through a catheter or the like connecting the pump mechanism to the infusion location. Accordingly, a further build up of pressure from multiple pump strokes within a relatively short period of time may be avoided.

In some infusion contexts, small blockages may occur, for example, in a catheter between the pump outlet and the infusion location, which obstruct the flow of infusion medium. Such blockages can cause a pressure differential within a pre-determined detectable range. According to yet a further embodiment, upon detection of a pressure differential corresponding to such a blockage, the power control electronics 30 increases the power applied to the coil to cause the pump mechanism to blow out the blockage or push medium through a small opening around or through the blockage. The power to the coil may be increased, for example, by adjusting the capacitor cut-off point 44 to increase the discharge time. In preferred embodiments, the power to the coil is increased for a single or a predefined number of pump strokes and is thereafter returned to the normal operating power. In further preferred embodiments, the power to the coil remains at its increased value until the detected pressure differential indicates that the blockage has been removed. In yet further embodiments, the power usage by the coil may be monitored by the patient's doctor (or other suitable technician) to determine whether or not a blockage is present and to take appropriate actions based on that determination.

In further infusion contexts, air bubbles may accumulate in the system, resulting in detectable changes in the pressure differential. Accordingly, embodiments may include control electronics 30 which, in response to such a detection, controls the operation of the pump mechanism to clear such bubbles and re-prime, for example, by causing the pump mechanism to make a predetermined number of strokes.

Similarly, the depletion of infusion medium in the pump reservoir can result in detectable changes in the pressure differential. Accordingly, embodiments may include control electronics 30 which includes a signaling device, such as a transmitter for transmitting a signal indicating that the reservoir is low, in response to such a detection.

Figure 6:
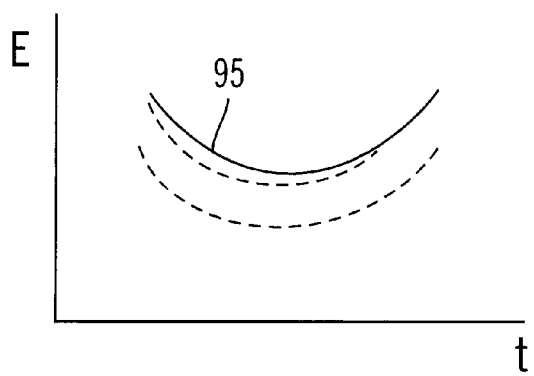
FIG. 6 is a graphical representation of example energy consumption characteristics of an electromagnetic pump mechanism.
Figure 7:
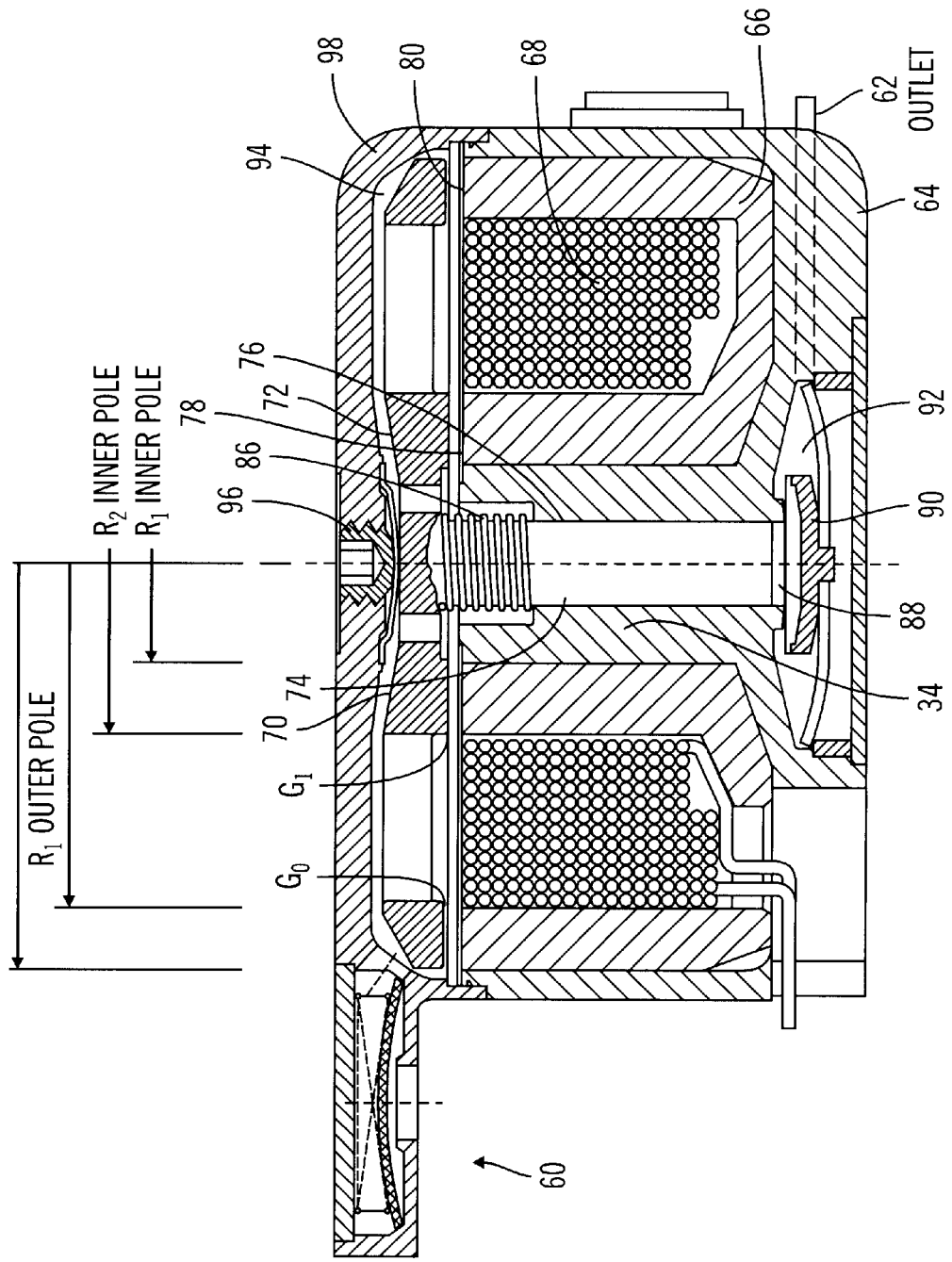
FIG. 7 is a cross-section view of one example embodiment of a pump mechanism, in a quiescent or retracted state.

In further embodiments, certain structural configurations of the pump mechanism 20 may be employed to improve energy utilization and power consumption efficiency. As noted above, a pump mechanism 20 may have a structure and operation according to embodiments as in co-pending U.S. patent application Ser. No. 60/317,886 (attorney docket no. 047711.0204), titled "Infusion Device And Driving Mechanism For Same," which is incorporated herein by reference. An example of that type of pump mechanism is shown in FIGS. 6 and 7. However, further embodiments may employ other suitable pump or drive mechanism configurations. In addition, various aspects described herein with respect to the pump mechanism shown in FIGS. 6 and 7 may be employed in other pump mechanism configurations having a coil and armature structure.

FIG. 6 shows a cross-sectional view of an embodiment of a pump mechanism in a retracted (or quiescent) state. FIG. 7 shows a cross-sectional view of the same pump mechanism embodiment, in a forward stroke state. The pump mechanism employs electromagnetic and mechanical forces to change (or move) between retracted and forward stroke states, to cause infusion medium to be drawn in through an inlet 60 and forced out of an outlet 62.

The pump mechanism of FIGS. 6 and 7 includes a housing 64, containing an annular coil cup 66 which holds a coil 68 (corresponding to coil 24 in FIGS. 2 and 3). The coil cup 66 is composed of a magnetically conductive material that forms a core to provide a path for the electromagnetic flux generated when the coil is energized. An actuator 70, composed of an armature 72 and a piston 74, is positioned with the piston 74 extending through a central channel 76 in the housing and with the armature 72 located adjacent the coil cup 66. The coil cup 66 surrounds the central channel 35 and defines a first pair of annular pole surfaces, including an inner pole surface 78 and an outer pole surface 80.

Figure 8:
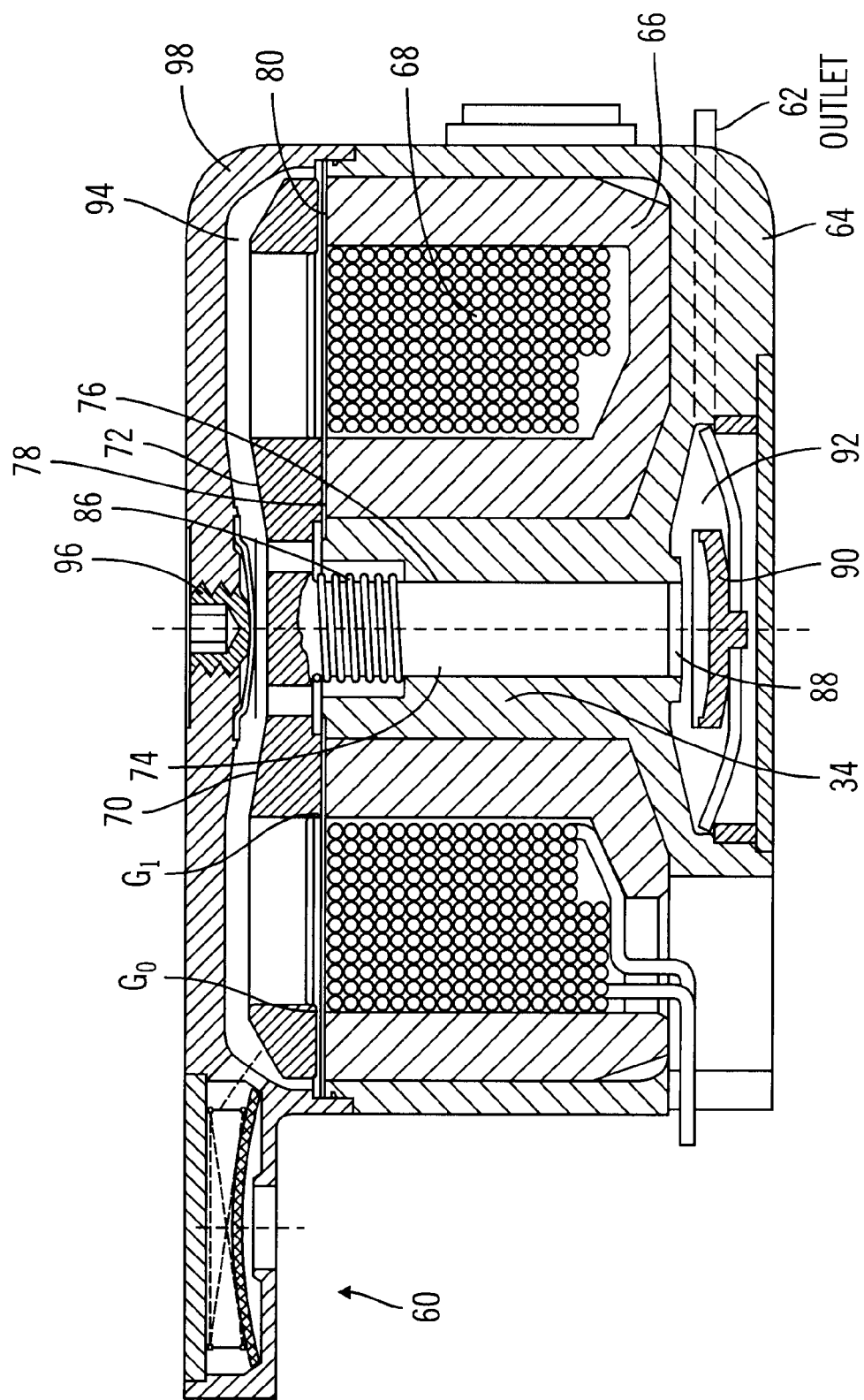
FIG. 8 is a cross-section view of the example pump mechanism embodiment of FIG. 7, in a forward stroke state.
Figure 9:
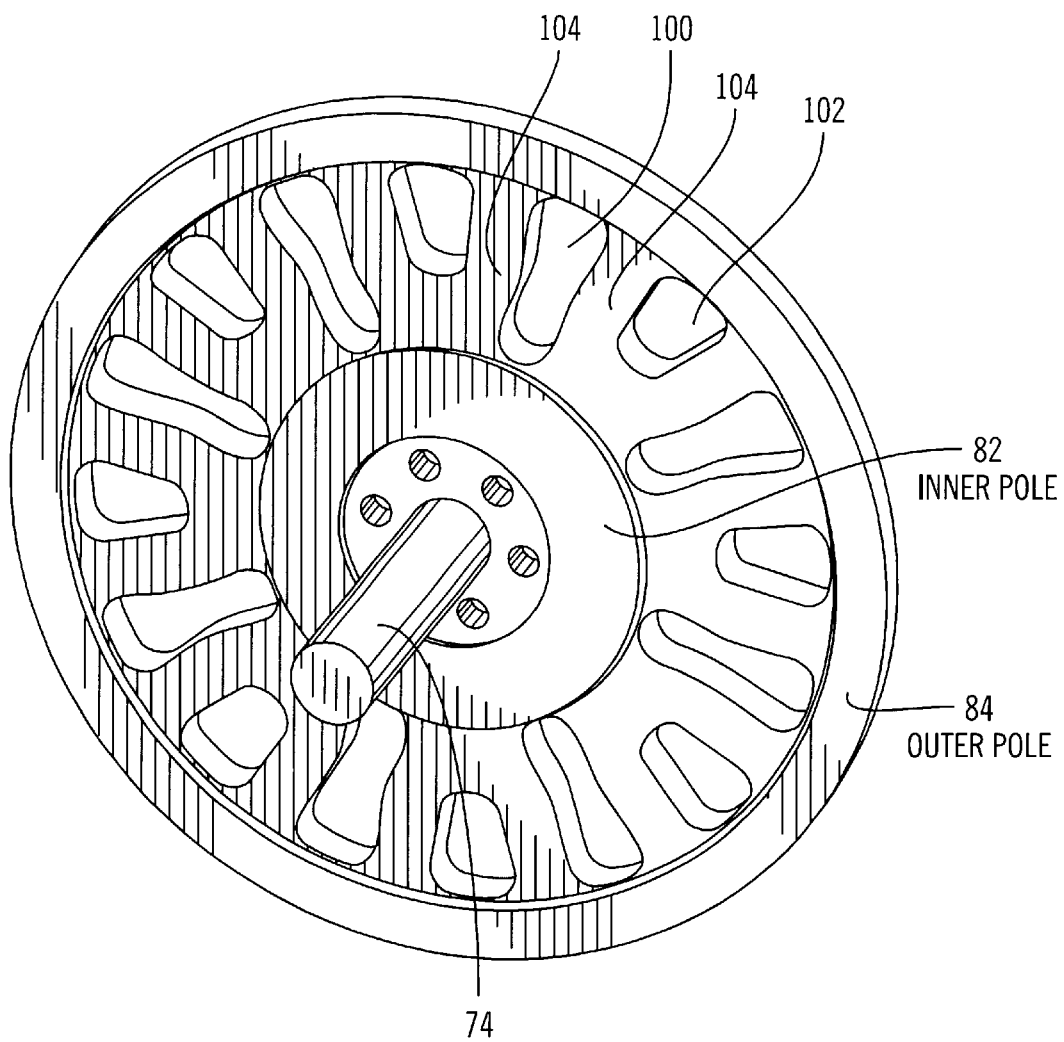
FIG. 9 is a perspective view of an actuator for a pump mechanism according to an embodiment of the invention.

The actuator 70 is also shown in FIG. 8. With reference to FIG. 8, the actuator 70 has a generally disc-shaped armature 72 composed of a magnetically conductive material that completes the flux path through the coil cup 66. The actuator includes a second pair of pole surfaces, including an inner pole surface 82 and an outer pole surface 84 which face the inner and outer pole surfaces 78 and 80 of the coil cup 66, respectively.

A spring 86 is positioned to bias the armature away from the coil cup to provide a gap between the first and second pairs of pole surfaces, when the pump mechanism is in the retracted state as shown in FIG. 6. By application of an electric power pulse to the coil 68, an electromagnetic field is produced, creating a flux path through the coil cup and armature, and across the gaps between the facing pole surfaces. The electromagnetic field forces the armature toward the coil cup and, thus, moves the actuator to the forward state shown in FIG. 7.

As the actuator moves from the retracted state (FIG. 6) to the forward state (FIG. 7), the piston 74 compresses a volume of infusion medium in a chamber 88. The compression force in the chamber 88 opens a valve 90 and forces the medium into an outlet chamber 92 and, eventually, through the outlet 62. After the electromagnetic field dissipates, the actuator is returned to its retracted position (FIG. 6) by the force of the spring 86. The return stroke causes the volume of the chamber 88 to increase, which reduces the chamber pressure and draws infusion medium from a chamber 94 at the inlet end of the pump into the chamber 88 for the next forward stroke. In this manner, the pump mechanism drives a defined volume of medium out of the outlet 62, each time a power pulse is applied to the coil 68.

Various aspects relating to structure of the pump mechanism of FIGS. 6 and 7 can affect the energy utilization and power consumption efficiency. Accordingly, preferred embodiments of the present invention improve or optimize one or more of such structural aspects for improved energy utilization and efficiency.

A graphical representation of an energy utilization curve 95 for a pump mechanism is shown in FIG. 6. In FIG. 6, the vertical axis represents energy, for example, in millijoules, while the horizontal axis represents the time required to complete a stroke. The energy curve tends to be higher at the beginning of the stroke, where a greater amount of energy is used to initiate actuator motion from a static state, and again at the end of the stroke, as the pressure within the pump mechanism increases during the forward stroke, as the pressure within the pump mechanism increases during the forward stroke. For improved power consumption efficiency, the pump mechanism structure may be configured to reduce or lower portions of the energy utilization curve, for example, as shown in the broken line curves of FIG. 6.

In one preferred embodiment, the ratio of the surface area of the outer poles to the surface area of the inner poles is selected to improve energy usage efficiency and, thus, lower the energy utilization curve. In the pump mechanism embodiment of FIGS. 6 and 7, the surface area of an annular pole is defined by:

$$2\pi R_2 - 2\pi R_1$$

where $R_2$ is the mean outer radius of the annular pole surface and $R_1$ is the mean inner radius of the annular pole surface.

In one embodiment, to achieve the above-noted desired ratio, the radial width of the inner poles may be greater than the radial width of the outer poles. The narrower outer poles produce less flux leakage or fringing than wider poles. Thus, by configuring the coil cup and armature with narrower outer poles, less leakage will occur at the outer periphery of the outer poles, where most leakage would otherwise tend to occur in the annular coil and core configuration. In this manner, a greater energy utilization efficiency may be achieved.

Further structural features may be employed to improve energy utilization efficiency. For example, the gaps between the poles may be selected to improve energy usage efficiency and, thus, lower the energy utilization curve.

In a preferred embodiment, the gap between the outer pole surfaces 80 and 84 is larger than the gap between the inner pole surfaces 78 and 82, when the actuator is in the retracted position, as shown in FIG. 6. The different gap sizes may be achieved, for example, by configuring the armature or the coil cup to space the inner poles closer together than the outer poles. In an example preferred embodiment, the ratio of the inner pole gap $G_I$ to the outer pole gap $G_o$ is selected to be within the range of from about 0.3 up to about 1.0 and, more preferably, is about 0.45.

The retracted state of the pole gaps $G_I$ and $G_o$ may be adjusted by an adjusting plunger 96 in a cover 98 over the armature. The adjusting plunger 96 may comprise a threaded member for contacting the armature 42 when the armature is in the fully retracted position shown in FIG. 3, to set the retracted position of the armature. In preferred embodiments, a seal may be disposed between the plunger 96 and the cover member 98, for example, but not limited to, a silicon rubber sealing ring. In further embodiments, a flexible diaphragm (such as, but not limited to, a thin titanium sheet or foil) may be coupled to the inside surface of the cover member 98 and sealed around the opening through which the plunger 96 extends. The diaphragm will flex to allow the plunger to define an adjustable retracted position and, yet, provide sealing functions for inhibiting leakage at the interface between the plunger 96 and the cover member 98. In further preferred embodiments, once a proper armature position is set, the plunger is fixed in place with respect to the cover member, for example, by adhering the plunger to the cover member with one or more welds, adhesives or other securing means.

Yet further structural features may be employed to improve energy utilization efficiency. For example, the armature 72 portion of the actuator may be provided with apertures and, in more preferred embodiments, a pattern of apertures as described below. An example of an aperture pattern is shown in FIG. 8. The apertures provide fluid flow paths through which infusion medium present in the chamber 94 may pass as the armature is moved between retracted and forward positions, shown in FIGS. 6 and 7, respectively. As a result, the armature experiences less fluidic resistance to its motion. In this manner, the energy required to initiate armature motion and to continue the armature motion from the retracted position (FIG. 6) to the forward position (FIG. 7) may be reduced, as compared to an armature structure without fluid flow apertures.

According to a further preferred embodiment, the armature is configured with a pattern of apertures, where the pattern is designed to provide sufficient fluid flow paths and also provide radially directed flux paths for the electromagnetic field produced when the coil 68 is energized. One example aperture pattern is shown in FIG. 8, wherein the openings include a plurality of larger openings 100 which are elongated in the radial dimension of the armature, and a plurality of smaller openings 102, each disposed between a pair of larger openings 100. The sections 104 of the armature 72 between the openings 100 and 102 define radial struts coupling an annular outer section (or outer pole 84) to an inner section (or inner pole 82) of the armature. Other embodiments of the invention may employ other suitable aperture patterns, preferably providing radial flux paths. In addition, other embodiments of the invention may employ an actuator without apertures.

Yet further structural features may be employed to improve energy utilization efficiency. For example, the aspect ratio of the coil may be selected to improve energy usage efficiency and, thus, lower the energy utilization curve. The coil 68 has a length dimension $L_c$ and a diameter dimension $D_c$, the ratio of which, or aspect ratio, is represented as $L_c/D_c$. In an example preferred embodiment, the aspect ratio of the coil is made relatively small (more preferably, less than 1) to reduce or minimize leakage flux.

Thus, embodiments of the invention may employ a pump mechanism having one or more features relating to structural configurations for improved power consumption efficiency. According to yet further embodiments, additional features may be provided to improve the efficient use of electric power from a depletable source, such as the battery 26 in FIG. 3. For example, with reference to FIG. 3, a power disconnect switch 41 may be provided between the capacitor and the battery, to allow the capacitor to be electrically disconnected from the battery during storage. The battery disconnect switch may be, for example, a manually operated switch which is opened (or turned OFF) by manual operation and does not require an active signal on a signal line to remain open (OFF). By opening (turning OFF) the battery disconnect switch 41 prior to storage or other periods of non-use, the system may avoid losing battery power due to the inherent leakage of the capacitor during such periods.

Another manner of improving the operational life of an infusion device according to embodiments of the invention is to reduce the number of operations of the drive mechanism required over a given period of time, by pumping reduced volumes of a higher concentration infusion medium (an infusion medium with a higher concentration of active ingredients) or pumping higher concentration volumes at reduced intervals. However, higher concentration mediums may require a greater precision in controlling the volume delivered to the patient during a drive operation, to avoid delivering too great or too small of a volume of the higher concentration medium to the patient. Accordingly preferred embodiments employ a pump mechanisms configuration which allows delivery of controlled volumes of infusion medium and, thus, to allow sufficiently precise delivery of relatively high concentration infusion medium. Examples of such pump mechanism configurations are described in co-pending U.S. patent application Ser. No. 60/317,886 (attorney docket no. 047711.0204), titled "Infusion Device And Driving Mechanism For Same," cited above, and are shown in FIGS. 6 and 7 herein.

Accordingly, a number of aspects and features relating to the power control system and pump mechanism configuration and operation described above can provide individually, or be combined to contribute to, the efficient use of power to, thereby, prolong the operational life of an electromagnetic pump mechanism. However, the foregoing description of preferred embodiments of the invention has been presented for the purposes of illustration and description. It is not intended to be exhaustive or to limit the invention to the precise forms disclosed. Many modifications and variations are possible in light of the above teaching.

What is claimed is:

1. An electronic control system for use with an electromagnetic pump having a coil that can be energized to produce a pump stroke, the electronic control system comprising:
   a power source;
   a capacitor connected to the power source for receiving a charge from the power source and connectable to the coil to selectively discharge power pulse signals to the pump coil for selectively energizing the pump coil;
   control electronics for controlling the capacitor to discharge for each power pulse signal.

2. An electronic control system as recited in claim 1, wherein the control electronics comprises a switch device connected on one side to the capacitor and connectable on the other side to the coil, and control signal electronics for providing a control signal to the switch device for selectively opening and closing the switch.

3. An electronic control system as recited in claim 2, wherein the switch device comprises a field effect transistor (FET).

4. An electronic control system as recited in claim 1, wherein the control electronics comprises an electronic circuit for cutting off the capacitor discharge prior to the end of the pump stroke.

5. An electronic control system as recited in claim 1, wherein the control electronics comprises a detector for detecting the end of a pump stroke and an electronic circuit for cutting off the capacitor discharge prior to the detected end of the pump stroke.

6. An electronic control system as recited in claim 5, wherein the detector for detecting the end of a pump stroke comprises an electronic circuit for detecting the (EMF) in the coil.

7. An electronic control system as recited in claim 1, wherein the control electronics comprises a pressure sensor for detecting a pressure differential in the pump and means for controlling the capacitor discharge based on the detected pressure differential.

8. An electronic control system as recited in claim 7, wherein said means controls the capacitor discharge to produce a power pulse for increasing power as the detected pressure differential increases and for decreasing power as the detected pressure differential decreases.

9. An electronic control system as recited in claim 1, wherein the power source comprises a depletable power source.

10. An electronic control system as recited in claim 1, wherein the power source comprises a battery.

11. An electronic control system as recited in claim 1, wherein the value of the capacitor is between about 500 micro Farad and about 3000 micro Farad.

12. An electronic control system as recited in claim 1, wherein the value of the capacitor is about 2000 micro Farad.

13. An electronic control system as recited in claim 1, wherein the voltage across the capacitor after a partial discharge to produce a power pulse is in the range of about 40% to about 90% of the voltage across the capacitor prior to the partial discharge.

14. An electronic control system as recited in claim 1, wherein the power source charges the capacitor to a fully charged state in which the voltage across the capacitor is in the range of about 1.8 volts to about 5.0 volts.

15. A system as recited in claim 1, wherein the control electronics operates to discharge the capacitor partially, but not fully, for each power pulse signal.

16. An electronic control system for use with an electromagnetic pump having a coil that can be energized to produce a pump stroke, the electronic control system comprising:
   a power control circuit connectable to the pump coil for providing electrical power to the pump coil to selectively energize the pump coil; and
   a detector for detecting the end of a pump stroke;
   wherein the power control circuit includes an electronic circuit for cutting off electrical power to the pump coil prior to the detected end of the pump stroke.

17. An electronic control system as recited in claim 16, wherein the power control circuit comprises a power source and a capacitor connected to the power source for receiving a charge from the power source and connectable to the coil to selectively discharge power pulse signals to the pump coil.

18. An electronic control system as recited in claim 16, wherein the power control circuit comprises a power source and a capacitor connected to the power source for receiving a charge from the power source and connectable to the coil to selectively discharge power pulse signals to the pump coil and wherein the electronic circuit for cutting off electrical power comprises a switch device connected on one side to the capacitor and connectable on the other side to the coil, and control signal electronics for providing a control signal to the switch device for selectively opening and closing the switch.

19. An electronic control system as recited in claim 18, wherein the electronic circuit for cutting off electrical power includes means for controlling the capacitor to discharge for each power pulse signal.

20. A system as recited in claim 19, wherein the means for controlling the capacitor operates to discharge the capacitor partially, but not fully, for each power pulse signal.

21. An electronic control system as recited in claim 16, wherein the detector for detecting the end of a pump stroke comprises an electronic circuit for detecting the back EMF in the coil.

22. An electronic control system as recited in claim 21, wherein the power control circuit includes means for comparing a detected back EMF with an historical record of back EMF detections.

23. An electronic control system for use with an electromagnetic pump having a coil that can be energized to produce a pump stroke, the electronic control system comprising:

a power control circuit connectable to the pump coil for providing electrical power pulse signals to the pump coil to selectively energize the pump coil, each power pulse signals having a definable amount of power; and a pressure sensor for detecting a pressure differential in the pump;

wherein the power control circuit includes an electronic circuit for controlling the amount of power of each power pulse signal based on the detected pressure differential, and wherein the power control circuit comprises a power source and a capacitor connected to the power source for receiving a charge from the power source and connectable to the coil to selectively discharge power pulse signals to the pump coil.

24. An electronic control system as recited in claim 21, wherein the electronic circuit for controlling the amount of power includes means for controlling the capacitor to increase the discharge period for each power pulse signal as the detected pressure differential increases and to decrease the discharge period for each pulse signal as the detected pressure differential decreases.

25. An electronic control system as recited in claim 23, wherein the power control circuit comprises a power source and a capacitor connected to the power source for receiving a charge from the power source and connectable to the coil to selectively discharge power pulse signals to the pump coil and wherein the electronic circuit for controlling the amount of power comprises a switch device connected on one side to the capacitor and connectable on the other side to the coil, and control signal electronics for providing a control signal to the switch device for selectively opening and closing the switch based on the detected pressure differential.

26. An electronic control system as recited in claim 23, wherein the electronic circuit for controlling the amount of power includes means for controlling the capacitor to discharge for each power pulse signal.

27. A system as recited in claim 26, wherein the means for controlling the capacitor operates to discharge the capacitor partially, but not fully, for each power pulse signal.

28. An electronic control system as recited in claim 23, wherein the power control circuit produce a power pulse for increasing power as the detected pressure differential increases and for decreasing power as the detected pressure differential decreases.

29. An electronic control system for use with an electromagnetic pump having a coil that can be energized to produce a pump stroke, the electronic control system comprising:

a power source;

a capacitor connected to the power source for receiving a charge from the power source and connectable to the coil to selectively discharge power pulse signals to the pump coil for selectively energizing the pump coil;

a switch device connected between the power source and the capacitor for selectively disconnecting the power source from the capacitor for periods of non-use.

30. An electronic control system as recited in claim 29, wherein the switch device comprises a switch capable of remaining in a disconnect state in which the capacitor is disconnected from the power source, without the continuous application of electrical power to the switch device.

31. An electronic control system as recited in claim 29, wherein the switch device comprises a manually operable switch.

32. A drive mechanism for delivery of infusion medium, the drive mechanism comprising:

an inlet for receiving infusion medium;

a coil that can be energized to produce a pump stroke;

an armature disposed adjacent the coil, and moveable between first and second positions to define a pump stroke, in response to an energization of the coil;

an outlet in flow communication with the outlet chamber, for discharging a volume of infusion medium with each pump stroke; and a power control circuit connected to the pump coil for selectively energizing the pump coil to produce stroke;

wherein the coil has an aspect ratio defined by the length of the coil divided by the diameter of the coil and wherein the coil aspect ratio is less than 1.

33. A drive mechanism for delivery of infusion medium, the drive mechanism comprising:

an inlet for receiving infusion medium;

a coil that can be energized to produce a pump stroke;

an armature disposed adjacent the coil, and moveable between first and second positions to define a pump stroke, in response to an energization of the coil;

an outlet in flow communication with an outlet chamber, for discharging a volume of infusion medium with each pump stroke; and a power control circuit connected to the pump coil for selectively energizing the pump coil to produce a pump stroke;

wherein the drive mechanism further comprises a coil core for providing a flux path upon energization of the coil, wherein the coil core defines an outer annular pole surface and an inner annular pole surface and the armature defines corresponding outer and inner annular pole surfaces, wherein the inner pole surfaces are separated by a first gap and the outer pole surfaces are separated by a second gap, and wherein the ratio of the first gap to the second gap is within the range of about 0.3 to about 1.0.

34. An infusion device comprising:

an electromagnetic pump having a coil that can be energized to produce a pump stroke;

a power source;

a capacitor connected to the power source for receiving a charge from the power source and connectable to the coil to selectively discharge power pulse signals to the pump coil for selectively energizing the pump coil; and control electronics for controlling the capacitor to discharge for each power pulse signal.

35. A device as recited in claim 34, wherein the control electronics operates to discharge the capacitor partially, but not fully, for each power pulse signal.

36. An infusion device comprising:

an electromagnetic pump having a coil that can be energized to produce a pump stroke;

a power control circuit connectable to the pump coil for providing electrical power to the pump coil to selectively energize the pump coil; and a detector for detecting the end of a pump stroke;

wherein the power control circuit includes an electronic circuit for cutting off electrical power to the pump coil prior to the detected end of the pump stroke.

37. An infusion device comprising:

an electromagnetic pump having a coil that can be energized to produce a pump stroke;

a power source;

a capacitor connected to the power source and to the pump coil for receiving a charge from the power source and for selectively discharging power pulse signals to the pump coil to selectively energize the pump coil;

a switch device connected between the power source and the capacitor for selectively disconnecting the power source from the capacitor for periods of non-use;

a power control circuit connected to the pump coil for providing electrical power pulse signals to the pump coil to selectively energize the pump coil, each power pulse signal having a definable amount of power; and a pressure sensor for detecting a pressure differential in the pump;

wherein the power control circuit includes an electronic circuit for controlling the amount of power of each power pulse signal based on the detected pressure differential.

38. An infusion device comprising:

an electromagnetic pump having a coil that can be energized to produce a pump stroke;

a power source;

a capacitor connected to the power source and to the pump coil for receiving a charge from the power source and for selectively discharging power pulse signals to the pump coil to selectively energize the pump coil; and a switch device connected between the power source and the capacitor for selectively disconnecting the power source from the capacitor for periods of non-use.

39. A method of controlling power to an electromagnetic pump having a coil that can be energized to produce a pump stroke, the method comprising:

connecting a power source to a capacitor to charge the capacitor;

selectively discharging the capacitor to the pump coil to selectively energize the pump coil; and controlling the capacitor to discharge for each power pulse signal.

40. A method as recited in claim 39, wherein controlling the capacitor comprises connecting a switch device between the capacitor and the coil, and providing a control signal to the switch device for selectively opening and closing the switch.

41. A method as recited in claim 40, wherein the switch device comprises a field effect transistor (FET).

42. A method as recited in claim 39, wherein controlling the capacitor comprises cutting off the capacitor discharge prior to the end of the pump stroke.

43. A method as recited in claim 39, further comprising:

detecting the end of a pump stroke; and cutting off the capacitor discharge prior to the detected end of the pump stroke.

44. A method as recited in claim 43, wherein detecting the end of a pump stroke comprises detecting the back EMF in the coil.

45. A method as recited in claim 39, further comprising:

detecting a pressure differential in the pump; and controlling the capacitor discharge based on the detected pressure differential.

46. A method as recited in claim 45, wherein controlling the capacitor discharge based on the detected pressure differential comprises controlling the capacitor discharge to produce a power pulse for increasing power as the detected pressure differential increases and decreasing power as the detected pressure differential decreases.

47. A method as recited in claim 39, wherein the capacitor is controlled to discharge partially, but not fully, for each power pulse signal.

48. A method of controlling power to an electromagnetic pump having a coil that can be energized to produce a pump stroke, the method comprising:

providing electrical power to the pump coil to selectively energize the pump coil;

detecting the end of a pump stroke; and cutting off electrical power to the pump coil prior to the detected end of the pump stroke.

49. A method as recited in claim 48, wherein providing electrical power comprises connecting a power source to a capacitor to charge the capacitor; and selectively discharging the capacitor to provide a power pulse signal to the pump coil to selectively energize the pump coil.

50. A method as recited in claim 49, wherein selectively discharging the capacitor comprises controlling the capacitor to discharge for each power pulse signal.

51. A method as recited in claim 50, wherein the capacitor is controlled to discharge partially, but not fully, for each power pulse signal.

52. A method as recited in claim 48, wherein detecting the end of a pump stroke comprises detecting the back EMF in the coil.

53. A method as recited in claim 52, wherein detecting the end of a pump stroke further comprises comparing a detected EMF with an historical record of EMF detections.

54. A method of controlling power to an electromagnetic pump having a coil that can be energized to produce a pump stroke, the method comprising:

providing electrical power pulse signals to the pump coil to selectively energize the pump coil, each power pulse signal having a definable amount of power;

detecting a pressure differential in the pump; and controlling the amount of power of each power pulse signal based on the detected pressure differential, wherein providing electrical power pulse signals comprises;

connecting a power source to a capacitor to charge the capacitor; and selectively discharging the capacitor to provide a power pulse signal to the pump coil to selectively energize the pump coil.

55. A method as recited in claim 49, wherein selectively discharging the capacitor comprises controlling the capacitor to increase its discharge period for each power pulse signal as the detected pressure differential increases and to decrease its discharge period for each pulse signal as the detected pressure differential decreases.

56. A method as recited in claim 49, wherein selectively discharging the capacitor comprises controlling the capacitor to discharge for each power pulse signal.

57. An electronic control system as recited in claim 54, wherein controlling the amount of power comprises producing a power pulse for increasing power as the detected pressure differential increases and for decreasing power as the detected pressure differential decreases.

58. A method as recited in claim 49, wherein the capacitor is controlled to discharge partially, but not fully, for each power pulse signal.

* * * * *